(12) United States Patent
Ueno et al.

(10) Patent No.: US 7,449,608 B2
(45) Date of Patent: Nov. 11, 2008

(54) NAPHTHOL DERIVATIVE AND CHARGE CONTROL AGENT COMPRISING THE SAME

(75) Inventors: Ryuzo Ueno, Nishinomiya (JP); Masaya Kitayama, Takarazuka (JP); Kenji Minami, Sennan (JP); Hiroyuki Wakamori, Hikami-gun (JP); Nobuhiro Yonetani, Nishinomiya (JP)

(73) Assignee: Ueno Fine Chemicals Industry, Ltd., Osaka-Fu (JP)

( * ) Notice: Subject to any disclaimer, the term of this patent is extended or adjusted under 35 U.S.C. 154(b) by 191 days.

(21) Appl. No.: 10/498,224

(22) PCT Filed: Dec. 10, 2002

(86) PCT No.: PCT/JP02/12907

§ 371 (c)(1), (2), (4) Date: Feb. 3, 2005

(87) PCT Pub. No.: WO03/050078

PCT Pub. Date: Jun. 19, 2003

(65) Prior Publication Data

US 2005/0119487 A1  Jun. 2, 2005

(30) Foreign Application Priority Data

Dec. 13, 2001  (JP) .............................. 2001-380057

(51) Int. Cl.
C07C 39/14 (2006.01)
G03G 9/00 (2006.01)
G03G 15/00 (2006.01)

(52) U.S. Cl. ............ 568/735; 430/108.1; 430/74; 585/400

(58) Field of Classification Search ............ 430/74, 430/108.1; 252/299.62; 585/400; 568/735
See application file for complete search history.

(56) References Cited

U.S. PATENT DOCUMENTS 4,110,375 A   8/1978 Papenfuhs et al.
5,244,596 A * 9/1993 Takiguchi et al. .......... 345/87
5,595,685 A * 1/1997 Takiguchi et al. ...... 252/299.61
5,776,984 A * 7/1998 Dellaria et al. ............ 514/605

FOREIGN PATENT DOCUMENTS

EP    0 778 501 A1    6/1997

(Continued)

OTHER PUBLICATIONS

Answer set 31 of 31 USPATFULL on STN, Assession No. 9376214, Takigudhi et al., "mesomorphic compound for use in Liquids Crystal Composition and Liquid Crystal Device and Apparatus using same", Abstract.*
P. Ananthakrishnanadar & G. Varghesedharumara, Kinetics of Reaction of Substituted Naphthoyl Chlorides with Aniline; Indian Journal of Chemistry, vol. 22B, May 1983, pp. 506-507.

(Continued)

Primary Examiner—Daniel M. Sullivan
Assistant Examiner—Yate' K Cutliff
(74) Attorney, Agent, or Firm—Sughrue Mion, PLLC

(57) ABSTRACT

The present invention provides a novel naphthol derivative represented by the following general formula (I).

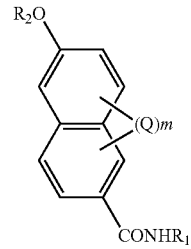

The novel naphthol derivative of the present invention is useful as a positively electrifiable charge control agent. The present invention further provides an electrophotographic toner comprising a charge control agent comprising the novel naphthol derivative represented by formula (I).

8 Claims, 9 Drawing Sheets

FOREIGN PATENT DOCUMENTS

| | | | |
|---|---|---|---|
| JP | 08-044114 | * | 2/1996 |
| JP | 8-44114 A | | 2/1996 |
| JP | 11-158135 A | | 6/1999 |
| WO | WO 94/23344 A1 | | 10/1994 |

OTHER PUBLICATIONS

Carlton Butler and Frank Albert Royle, Hydroxynaphthoic acids. Part II, Journal of the Chemical Society, Transactions, 123, 1649-57 (1923).

* cited by examiner

NAPHTHOL DERIVATIVE AND CHARGE CONTROL AGENT COMPRISING THE SAME

TECHNICAL FIELD

The present invention relates to a novel naphthol derivative and a charge control agent comprising the same. The present invention also relates to electrophotographic toner comprising the charge control agent.

BACKGROUND ART

Developers used in electrophotographic systems such as copying machine include two-component developer, which comprises carrier and toner, and single component developer, which contains no carrier. Conventional toners used in both developers are fine particles of binder resin in which colorants, such as pigment and dye, are dispersed.

One of the important properties of the toners is triboelectric chargeability. Properties required for toners include that they can generate a suitable amount of positive or negative electrostatic charge upon contacting with the carrier or charge providing device, and the amount of the charge is stable during continuous use or under an adverse environment. Binder resin, the main component of the toner may be triboelectrically chargeable but the amount of the generated electrostatic charge is not sufficient, and therefore image fogging may occur to make the resulting image unclear. In order to impart further triboelectric charging property, toners in general are added with a charge control agent so that the electrostatic charge is controlled suitably.

In these days, devices for electrophotographic process such as copying machine with organic photo conductor (OPC) are increasing. Such devices meet the demands for downsizing and lower prices. The organic photo conductors include positively charged type and negatively charged type, and the positively charged type is especially increasing because the amount of ozone generated upon charging is relatively small.

In addition, with regard to recent digital electrophotographic machines or laser beam printers, the reversal development system wherein images are developed using toners homopolar to the photo conductor becomes predominate. When the reversal development system using positively charged type organic photo conductor is employed, it is necessary to use the positively electrifiable toner.

As positive charge control agents used for positive electrophotographic toners, nigrosin dyes and quaternary ammonium bases and the likes are known and have been in practical use.

Problem to be Solved by Invention

However, there are some drawbacks that nigrosin dyes are black and therefore not suitable for color toner and that quaternary ammonium salts themselves are expensive and give low charging level. As such, positively electrifiable charge control agents that do not affect the colors of toners and give satisfactory charging level have been desired.

To solve the above-described problems, an object of the present invention is to provide a novel naphthol derivative which is suitably used as charge control agent for a positively electrifiable electrophotographic toner and the like.

Another object of the present invention is to provide a positive charge control agent having a good chargeability, an excellent dispersibility and compatibility with binder resins as well as being safe for human bodies and environments, and then be able to be applied for color toners.

Further object of the present invention is to provide a positive electrophotographic toner which can be charged uniformly within a short time period and shows a stable charging level over time. Said toner provides high quality images with high image density and less fogging.

Means for Solving the Problem

The present inventors have successfully synthesized a novel naphthol derivative starting from 2-hydroxynaphthalene-6-carboxylic acid and evaluated its properties, and then found that it has good positive electrifiablity and is suitable for a charge control agent of electrophotographic toner, and have completed the invention.

Accordingly, the present invention provides a novel naphthol derivative represented by formula (I):

wherein $R_1$ is selected from the group consisting of an optionally branched and optionally substituted aliphatic C1 to C20 hydrocarbon group which may have an unsaturated bond, an optionally substituted aromatic group, an optionally substituted condensed polycyclic hydrocarbon group and an optionally substituted heterocyclic group having conjugated double bonds;

$R_2$ is selected from the group consisting of hydrogen atom, alkaline metal, an optionally branched, optionally substituted C1 to C6 alkyl and acyl group and phenylalkyl group;

Q is selected from the group consisting of an optionally branched C1 to C6 alkyl and alkoxy group, halogen atom, nitro group, nitroso group, amino group and sulfo group; and m is an integer of 0 to 3.

The novel naphthol derivative of the present invention is suitably used as a charge control agent applied for electrophotographic toner and the like. Thus the present invention further provides a charge control agent comprising the naphthol derivative as well as an electrophotographic toner comprising the charge control agent.

DETAILED DESCRIPTION OF INVENTION

In the novel naphthol derivative of the present invention represented by the formula (I), examples of optionally branched and optionally substituted aliphatic C1 to C20 hydrocarbon groups which may have an unsaturated bond of $R_1$ include alkyl group such as methyl, ethyl, propyl, butyl, pentyl, hexyl, octyl, decyl, dodecyl and octadecyl; and C2 to C6 alkenyl group such as vinyl, allyl, propylenyl, butylenyl, pentylenyl, hexylenyl, octylenyl, dodecylenyl and octadecylenyl. Examples of optionally substituted aromatic groups include phenyl group, naphthyl group, anthryl group, anthraquinonyl group, and pyrenyl group. Examples of optionally substituted condensed polycyclic hydrocarbon groups include indenyl group, fluorenyl group, acenaphthenyl group, acenaphthylenyl group and perillenyl group. Examples of optionally substituted heterocyclic groups having conjugated double bonds include benzimidazolonyl group, carbazolyl group, pyridyl group, thiazolyl group, benzothiazolyl group, imidazolyl group, indolyl group, thiofuryl group, phenothiazinyl group, acridinyl group and quinolinyl group.

Examples of substituents in each definition may include halogen atom, halogenated lower alkyl, nitro, lower alkyl, lower alkoxy such as methoxy, cyano, phenyl, naphthyl, phenoxy, furyl, amino, toluidinylamino, triazinylamino, pyridinylamino, benzoylamino, sulfo, hydroxy, esterified carboxyl group such as alkoxycabonyl and phenoxycarbonyl, amidized carboxyl groups such as phenylcarbamoyl group, alkylaminosulfonyl group and alkenyl group of 2-6 carbon atoms which may include aryl group.

When the substituent contains an aromatic ring, the compound may further have one or more substituents such as halogen atom, nitro, lower alkyl, lower alkoxy, phenyl and cyano on said aromatic ring.

In the present specification and claims, "lower" represents a group having 1-6 carbon atoms.

"Aromatic group" represents a 6-membered monocyclic aromatic group or condensed ring group consisting of up to 4 of 6-membered aromatic rings.

"Condensed polycyclic hydrocarbon group" represents a group selected from the group consisting of indenyl group, fluorenyl group, acenaphtenyl group, acenaphthylenyl group and perillenyl group.

"Heterocyclic group having conjugated double bonds" represents a 5- or 6-membered mono-cyclic group or condensed heterocyclic group having at least one heteroatom selected from N, S and O and conjugated double bonds. When it represents a condensed ring group, said group may have up to 6 rings.

In the naphthol derivative of the present invention, a derivative wherein $R_1$ is an optionally branched and optionally substituted aliphatic hydrocarbon group having 9 to 20 especially 12 to 18 carbon atoms is preferable. Said derivative is suitable as a charge control agent because of its excellent chargeability. Among them, the compound of which $R_1$ is dodecyl group or octadecyl group is especially preferable.

The naphthalene ring of the naphthol derivative represented by formula (I) may have substituent(s) Q. Q is optionally selected from the group consisting of optionally branched alkyl and alkoxy group having 1 to 6 carbon atoms, halogen atom, nitro group, nitroso group, amino group and sulfo group.

The number of the substituent, "m", is usually 0, but may be up to 3.

$R_2$ is selected from the group consisting of hydrogen atom, alkaline metal, optionally branched and optionally substituted C1 to C6 alkyl and acyl group and phenylalkyl group.

The charging level of the naphthol derivative of the present invention was measured by the blow-off method describer below, and it was shown that the derivative was positively charged and the amount of the charge was no less than +2.0 μC/g, preferably no less than +10.0 μC/g. Examples of the naphthol derivative of the present invention include following compounds:

Among the above, the compound of (i) has especially good positive chargeability, and it is most suitable as a charge control agent of positive toners.

The naphthol derivative of the present invention can be, for example, prepared by the following method.

Firstly, reacting 2-naphthol with potassium hydroxide to give potassium 2-naphthol which is reacted with carbon dioxide under increased pressure followed by separation by acid crystallization and optionally purification to give a starting material, 2-hydroxynaphthalene-6-carboxylic acid.

Then, the resulting 2-hydroxynaphthalene-6-carboxylic acid is reacted with acid anhydride corresponding to the desired acyl group in an organic acid in order to acylate the hydroxy group to give 2-acyloxynaphthalene-6-carboxylic acid.

The resulting acid is reacted with thionyl chloride or the like in solvent such as xylene, sulfolane, tetrahydrofuran to give acid chloride which is reacted with amine to give a 6-amido derivative of 2-acyloxynaphthalene. Alternatively, acid chloride may be directly reacted with amine by using phosphorus trichloride or dicyclohexyl carbodiimide to give 6-amido derivative of 2-acyloxynaphthalene.

6-amido derivative of 2-hydroxynaphthalene may be obtained by reacting 6-amido derivative of 2-acyloxynaphthalene with base such as sodium hydroxide in hydroalcohol solvent, followed by neutralizing the reaction liquid with acid such as hydrochloric acid to give a precipitation which is then filtrated, washed and dried.

6-amido derivative of 2-alkoxynaphthalene can be obtained by dissolving 6-amido derivative of 2-hydroxynaphthalene in dimethylformamide to which halogenated alkyl and potassium carbonate are added and reacted followed by adding water to the resulting reaction liquid and filtrating, washing and drying the precipitate.

The naphthol derivative of the present invention is positively electrificated well and has good compatibility with resins, and therefore, can be dispersed uniformly in the resin. Furthermore, the compound exhibits only slight white color or is almost colorless, and therefore, the compound will not interfere with the color of the colorant used for color toner and the like.

In addition, the compound of the present invention can be synthesized by a simple process with low cost. It is safe for human body or environment because it does not contain metal. Accordingly, it exhibits excellent properties as charge control agent for electrophotographic toner, especially as charge control agent for positive toner.

Details of electrophotographic toner comprising the naphthol derivative of the present invention as a charge control agent are described bellow. In general, electrophotographic toners are prepared by dispersing additives such as colorant and charge control agent in the binder resin. The toner of the present invention can be manufactured in a manner similar to the conventional method for preparing toner using the naphthol derivative of the present invention as a charge control agent.

Binder resin used in the toner of the present invention may be any of those used in conventional electrophotographic toner. Examples of such resins include styrene polymer, acrylic polymer, styrene acrylic copolymer, styrene methacrylate ester copolymer, styrene propylene copolymer, styrene butadiene copolymer, styrene maleate copolymer, olefin resin, polyester resin, epoxy resin, polyurethane resin, polyvinyl butyral resin. These resins may be used alone or in combination.

As colorant, any conventional colorant used for electrophotographic toner can be preferably used. Examples of colorants include carbon black, lamp black, iron black, ultramarine blue, nigrosin dye, aniline blue, phthalocyanine blue, phthalocyanine green, Hansa yellow, chrome yellow, rose bengal, triallyl methane dye, monoazo and bisazo dye and pigment. The colorant may be chosen to give an intended color of the toner.

The colorant may be added to the binder resin preferably in an amount of 1-20 parts by weight, especially 2-10 parts by weight to 100 parts by weight of the binder resin.

The toner of the present invention comprises the naphthol derivative represented by formula (I) as a charge control agent. The naphthol derivative of formula (I) may be added to the binder resin preferably in an amount of 0.1-10 parts by weight, especially 0.1-5 parts by weight to 100 parts by weight of the binder resin. When the amount of the charge control agent is less than 0.1 parts by weight, the resulting toner may not have enough chargeability, and when the amount is more than 10 parts by weight, the quality of the toner tends to be detracted.

In the electrophotographic toner of the present invention, with the naphthol derivative of formula (I), other known positive charge control agent such as nigrosin dye and quaternary ammonium salt may be admixed as additional charge control agents.

The toner of the present invention may further comprise additives used for manufacturing conventional toners, for example, mold-releasing agent, external additives and the like. As mold-releasing agent, low molecular weight olefin polymer may be suitably used. Examples of external additives, which improve flowability, cleaning property, shelf stability of the toner, include inorganic fine particles such as silica, alumina and titanium oxide.

The particle size of toner is not specifically limited, but is preferably no more than 20 μm, especially no more than 10 μm.

The electrophotographic toner of the present invention may be manufactured by any known method. For example, but not limited to, the method wherein the above described ingredients are pre-kneaded uniformly by means of dry blender, Henschel mixer, ball mill or the like; the obtained mixture is melt and kneaded by means of a kneading machine such as Bunbury mixer, roll extruder and single- or twin-axis extruder kneader; the uniformly kneaded matter is cooled and pulverized; and if desired, classified, and then added with the external additives to give the toner may be employed. Alternatively, any known methods such as polymerizing method, microcapsule polymerizing method and spray dry method may be employed for the manufacture.

The charge control agent of the present invention exhibits good compatibility with resins and therefore, the agent can be admixed into the binder resin together with the other ingredients to give uniformly and stably chargeable toners with ease by means of molten kneading. The charge control agent of the present invention may be fixed or embedded on the surface or the area adjacent to the surface to the fine particles comprising binder resin and a colorant by means of a known method using mechanical impact to give toner.

The electrophotographic toner of the present invention comprising the naphthol derivative of the present invention as a charge control agent can be uniformly charged within a short time period and the charging property is stable over time. Accordingly, by using the toner of the present invention, high quality images with high image density and less fogging can be provided. Further, since the charge control agent has good compatibility with resins, it does not easily depart from the toner. Moreover, stain of the development sleeves and carriers with the charge control agent is effectively reduced and therefore, the toner can provide high-density image which is stable over continuous copying. In addition, the charge control agent of the present invention has less impact on the resulting color and therefore, useful for manufacturing color toners.

EXAMPLES

The present invention is further described in reference to the following example. The following examples are intended to illustrate the invention and are not to be intended to be construed to limit the scope of the invention.

Example 1

18.8 g of 2-hydroxynaphthalene-6-carboxylic acid was reacted with 94 g of acetic anhydride in 94 g of acetic acid at 80° C. for 4 hours. The reaction liquid was poured to 500 g of water and the precipitate was filtrated and washed thoroughly with methanol and water and then dried to give 22.3 g of 2-acetoxynaphthalene-6-carboxylic acid.

Figure 1:
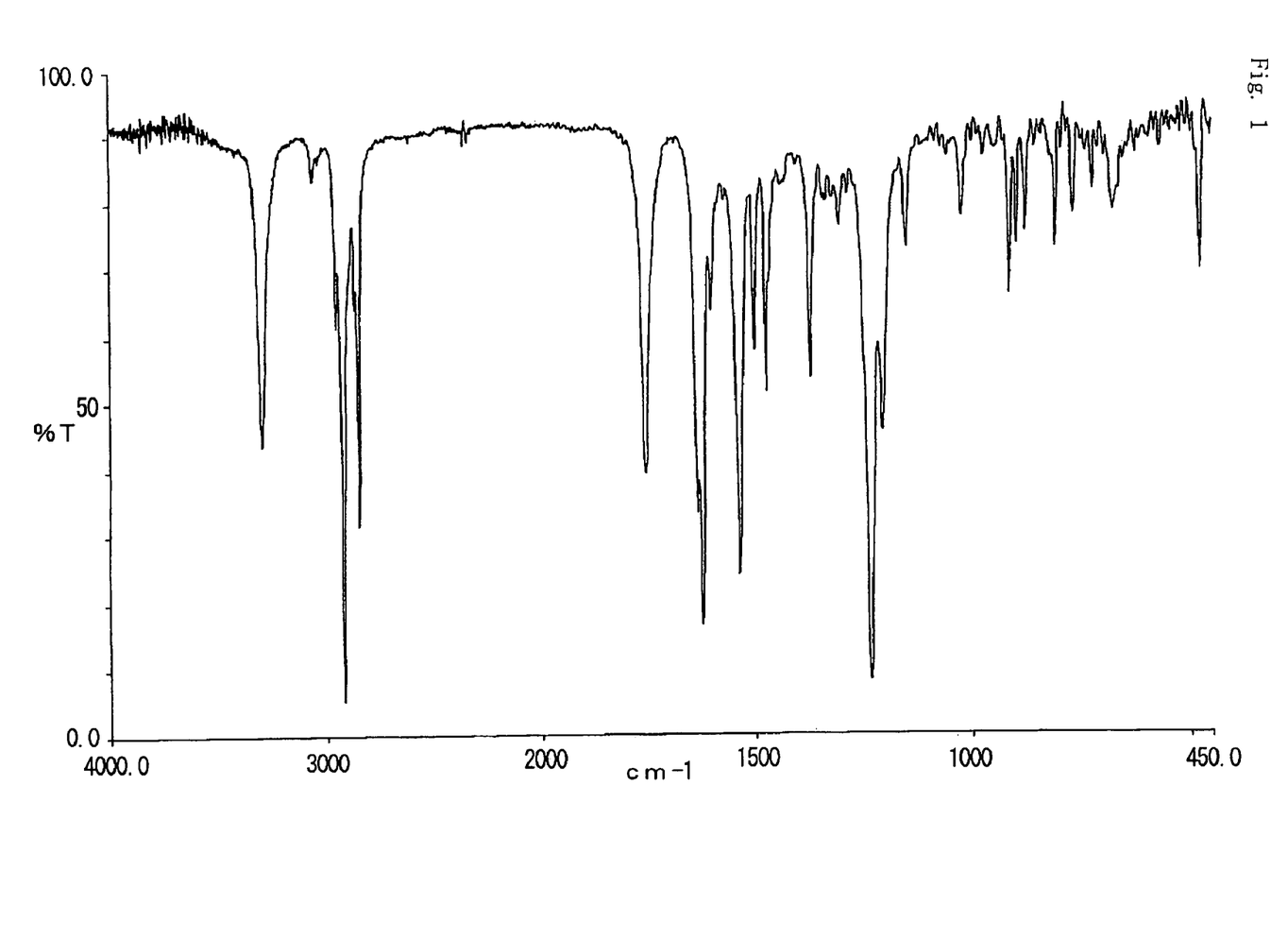
FIG. 1 is an infrared absorption spectrum (KBr) of the compound obtained in Example 1.

Thus obtained 22.3 g of 2-acetoxynaphthalene-6-carboxylic acid was reacted with 17.3 g of thionyl chloride in tetrahydrofuran at 40° C. for 2 hours. The excess thionyl chloride in the resulting reaction liquid was distilled out under reduced pressure, then 36.0 g of n-dodecyl amine was added to allow the reaction at 65° C. for 8 hours. Tetrahydrofuran in the reaction liquid was distilled out under reduced pressure, and to which 223 g of acetic acid was added. The resulting suspension was dissolved by heating to 80° C., and to which the 223 g of water was added. After cooling to room temperature, the precipitate was filtered, washed thoroughly with methanol and water and dried to give 30.1 g of 2-acetoxy-6-n-dodecyl aminocarbonylnaphthalene (decomposition point: 315° C.). The infrared absorption spectrum (KBr) of the compound is shown in FIG. 1.

The triboelectric charge of thus obtained 2-acetoxy-6-n-dodecyl aminocarbonylnaphthalene was measured by means of blow-off powder electrostatic charge tester (#TB200, Toshiba Chemical Corp, Tokyo, Japan) using metal mesh of 200-mesh (75 μm) under the condition showing below. The resulting triboelectric charge was +17.7 μC/g.

Measurement Conditions:
Temperature: 20° C.
Relative Humidity: 20%
Blow gas: ($N_2$, 0.1 MPa (G))
Blow-off time: 60 seconds Example 2

Figure 2:
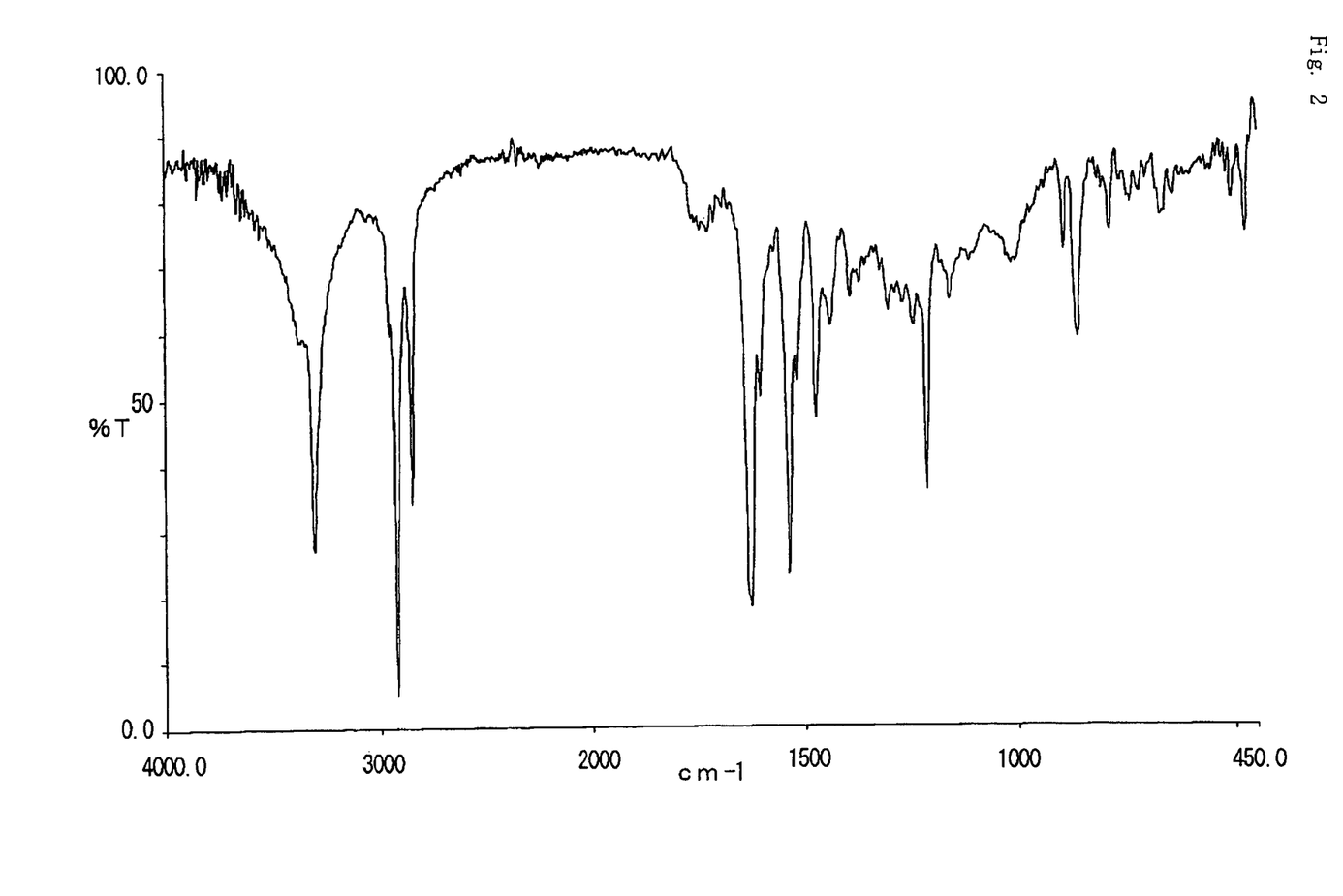
FIG. 2 is an infrared absorption spectrum (KBr) of the compound obtained in Example 2.

8.0 g of 2-acetoxy-6-n-dodecyl aminocarbonylnaphthalene obtained in Example 1 was suspended in 64 g of 50% methanol-water. To the suspension, 3.4 g of 48% sodium hydroxide aqueous solution was added and allowed to react at 60° C. for 1 hour. The reaction liquid was neutralized with 5% hydrochloric acid and stirred for 30 minutes and then precipitation was filtrated, washed thoroughly with methanol and water, dried to give 6.8 g of 2-hydroxy-6-n-dodecyl aminocarbonylnaphthalene (decomposition point: 329° C.). The infrared absorption spectrum (KBr) of the compound is shown in FIG. 2. The triboelectric charge was measured by blow-off method as described in example 1. The triboelectric charge of the compound was +6.7 μC/g.

Example 3

Figure 3:
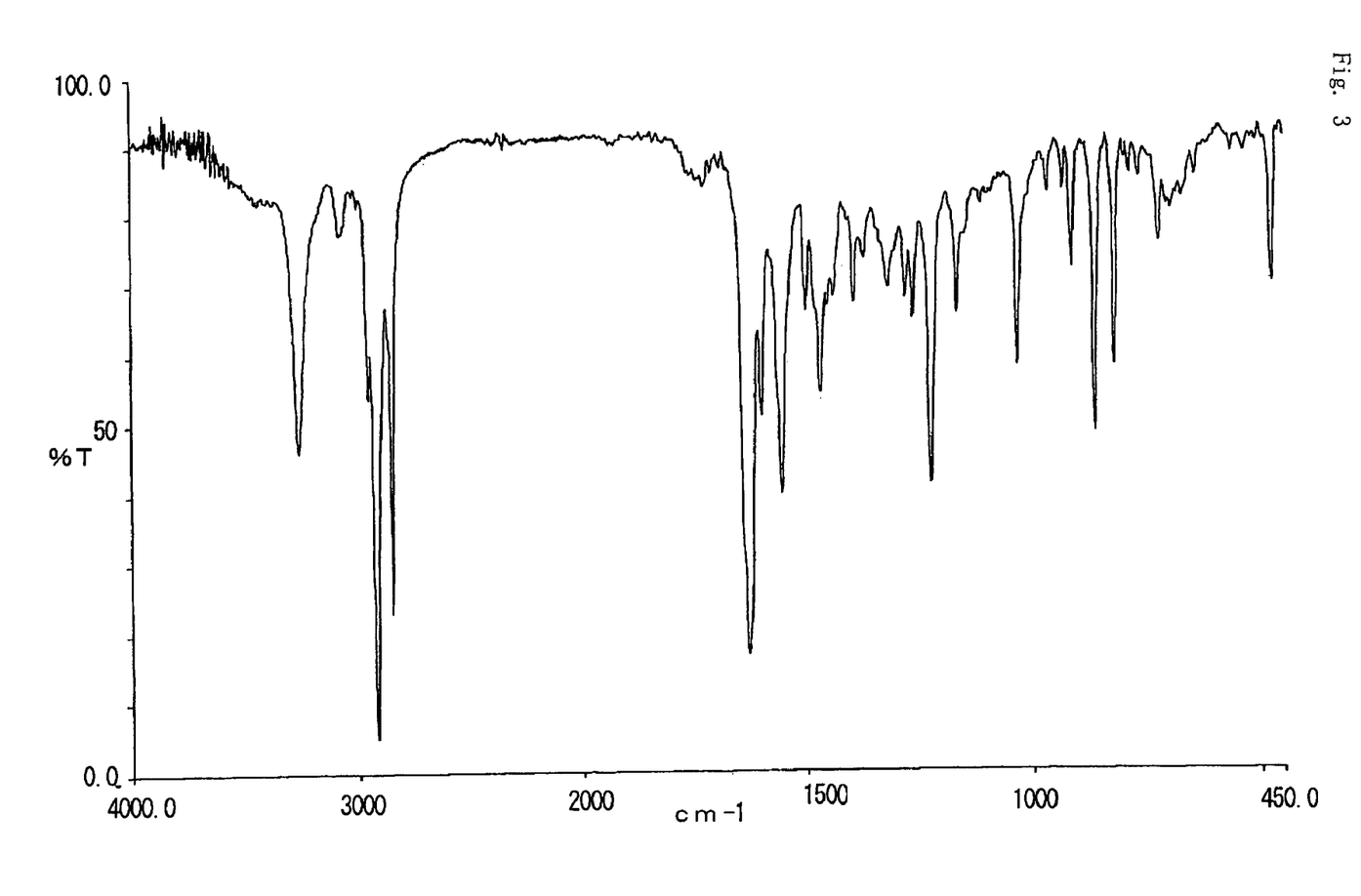
FIG. 3 is an infrared absorption spectrum (KBr) of the compound obtained in Example 3.

3.6 g of 2-hydroxy-6-n-dodecyl aminocarbonylnaphthalene obtained in example 2 was dissolved in 36 g of dimethylformamide. To this solution, 1.7 g of potassium carbonate and 2.2 g of methyl iodide were added, and allowed to react at 40° C. for 8 hours. The reaction liquid was poured to 180 g of water, and then precipitate was filtrated, washed thoroughly with methanol and water, dried to give 3.1 g of 2-methoxy-6-n-dodecyl aminocarbonylnaphthalene (Decomposition point: 324° C.). The infrared absorption spectrum (KBr) of the compound is shown in FIG. 3. The triboelectric charge was measured by blow-off method as described in example 1. The triboelectric charge of the compound was +17.6 μC/g.

Example 4

Figure 4:
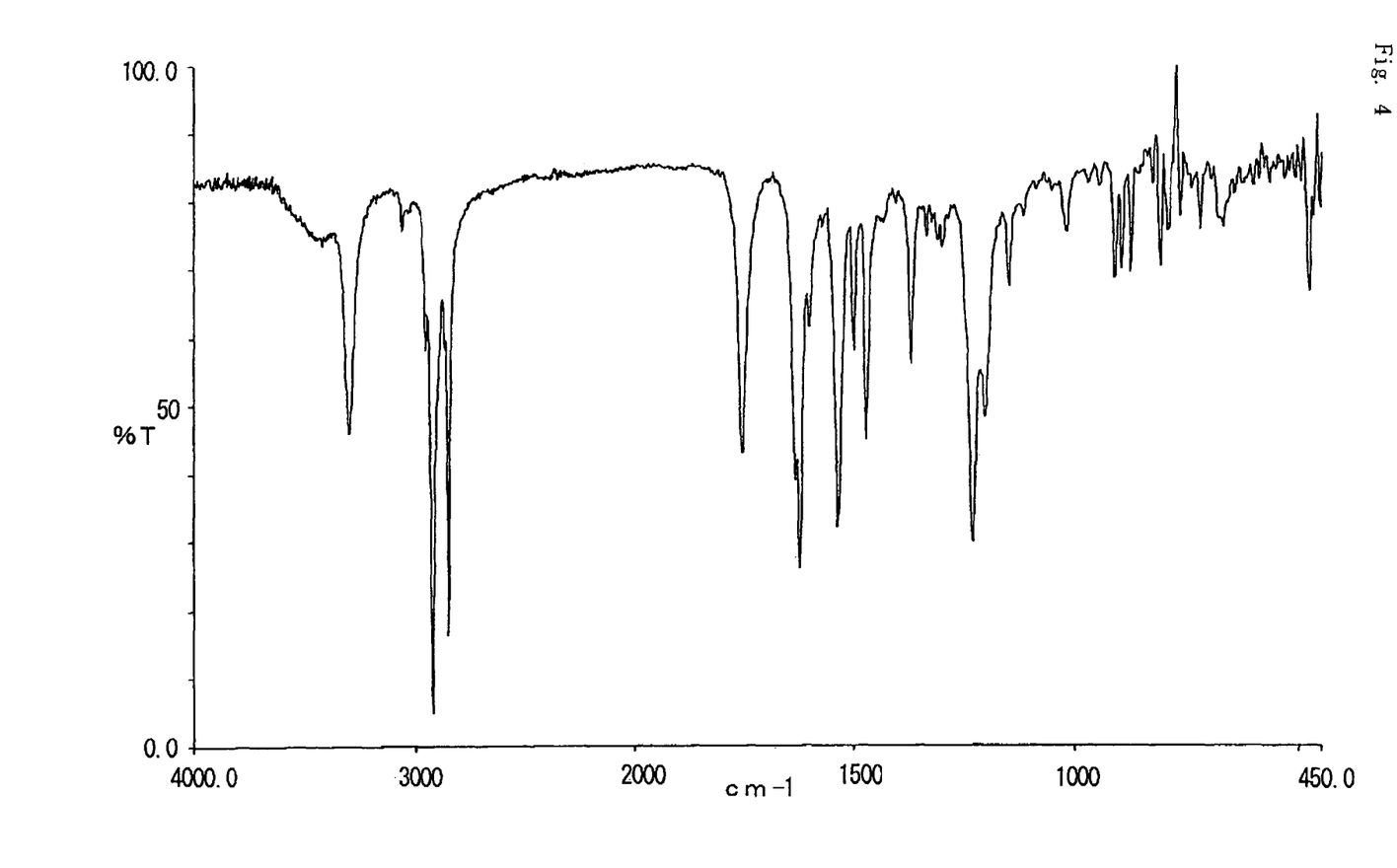
FIG. 4 is an infrared absorption spectrum (KBr) of the compound obtained in Example 4.

25.2 g of 2-acetoxy-6-n-octadecyl aminocarbonylnaphthalene (Decomposition point: 332° C.) was obtained according to the same method as example 1 with the exception that 52.3 g of n-octadecyl amine was used instead of 36.0 g of dodecyl amine in example 1. The infrared absorption spectrum (KBr) of the compound is shown in FIG. 4. The triboelectric charge was measured by blow-off method as described in example 1. The triboelectric charge of the compound was +5.9 μC/g.

Example 5

Figure 5:
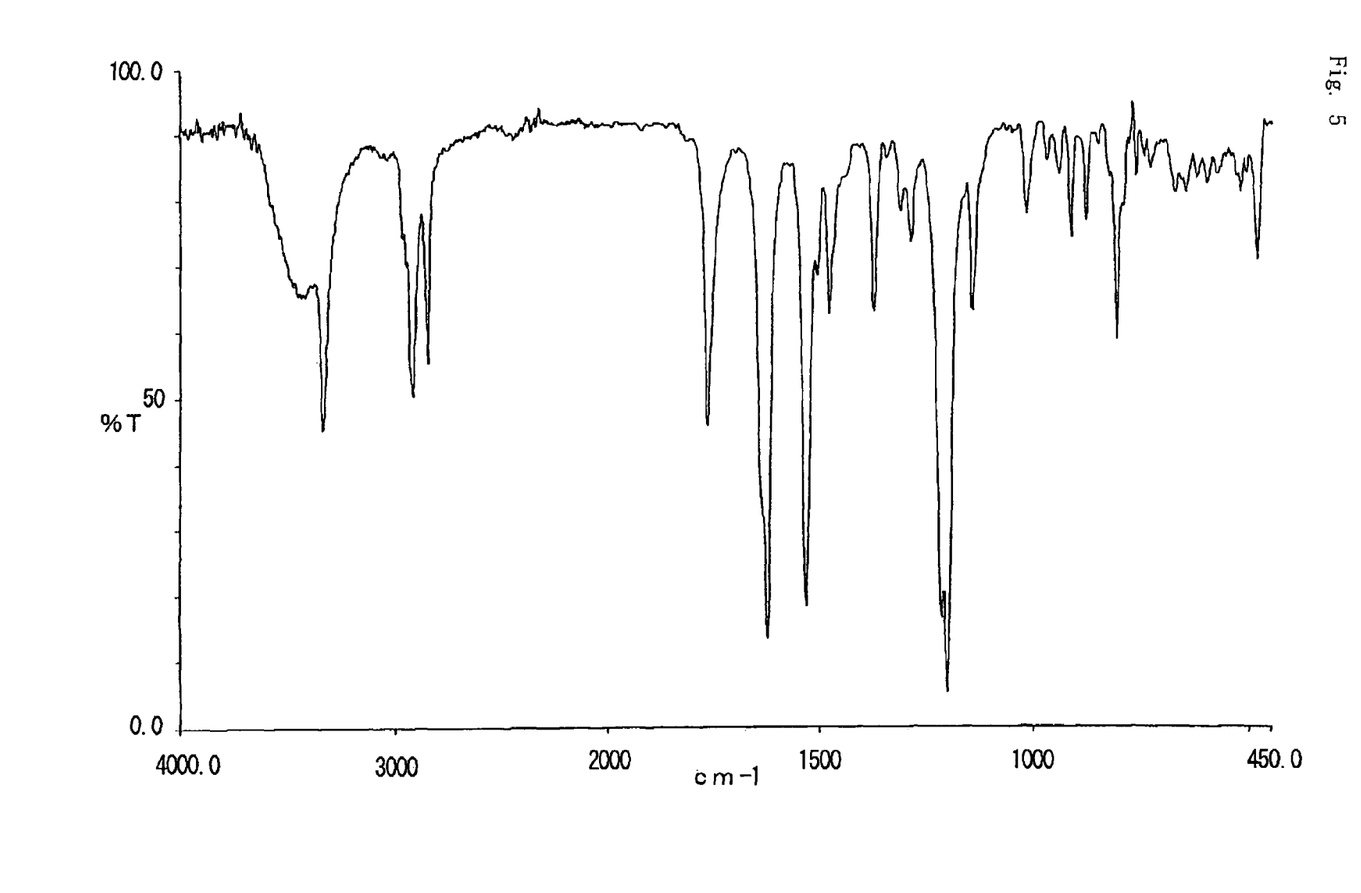
FIG. 5 is an infrared absorption spectrum (KBr) of the compound obtained in Example 5.

27.1 g of 2-acetoxy-6-n-octyl aminocarbonylnaphthalene (Decomposition point: 293.2° C.) was obtained according to the same method as example 1 with the exception that 25.1 g of n-octyl amine was used instead of 36.0 g of n-dodecyl amine in example 1. The infrared absorption spectrum (KBr) of the compound is shown in FIG. 5. The triboelectric charge was measured by blow-off method as described in example 1. The triboelectric charge of the compound was +2.8 μC/g.

Example 6

25.8 g of 2-acetoxy-6-phenyl aminocarbonylnaphthalene was obtained according to the same method as example 1 with the exception that 13.6 g of aniline was used instead of 36.0 g of n-dodecyl amine in example 1.

21.2 g of 2-hydroxy-6-phenyl aminocarbonylnaphthalene was obtained by the same method as example 2 with the exception that 25.8 g of 2-acetoxy-6-phenyl aminocarbonylnaphthalene was used instead of 8.0 g of 2-acetoxy6-n-dodecyl aminocarbonylnaphthalene in example 2.

Figure 6:
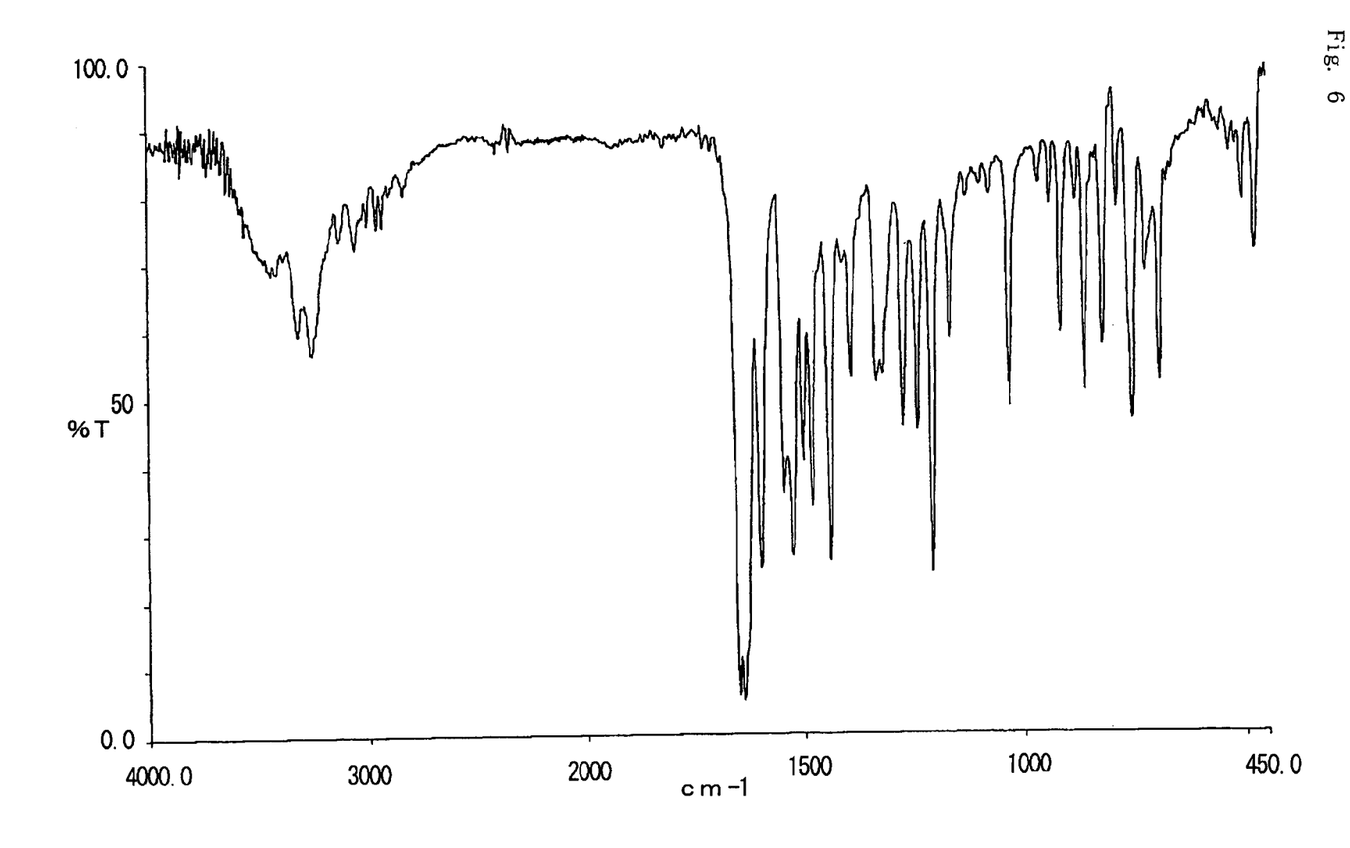
FIG. 6 is an infrared absorption spectrum (KBr) of the compound obtained in Example 6.

6.6 g of 2-methoxy-6-phenyl aminocarbonylnaphthalene (Decomposition point: 303.3° C.) was obtained by the same method as example 3 with the exception that 7.1 g of 2-hydroxy-6-phenyl aminocarbonylnaphthalene was used instead of 3.6 g of 2-hydroxy-6-n-odecyl aminocarbonylnaphthalene in example 3. The infrared absorption spectrum (KBr) of the compound is shown in FIG. 6. The triboelectric charge was measured by blow-off method as described in example 1. The triboelectric charge of the compound was +4.0 μC/g.

Example 7

Figure 7:
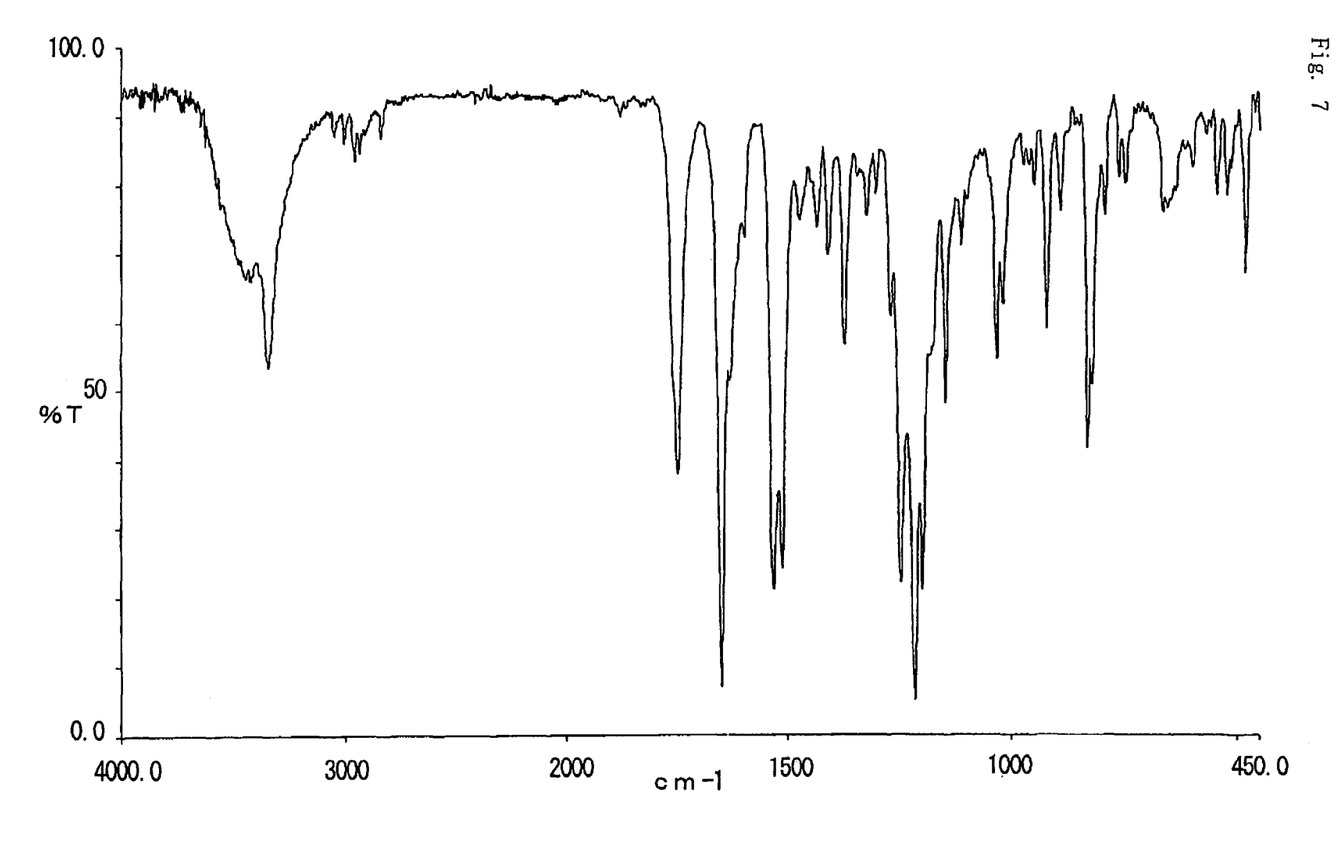
FIG. 7 is an infrared absorption spectrum (KBr) of the compound obtained in Example 7.

26.0 g of 2-acetoxy-6-(4-methoxyphenyl aminocarbonyl) naphthalene (Decomposition point: 311.5° C.) was obtained by the same method as example 1 with the exception that 17.9 g of p-anisidine was used instead of 36.0 g of n-dodecyl amine in example 1. The infrared absorption spectrum (KBr) of the compound is shown in FIG. 7. The triboelectric charge was measured by blow-off method as described in example 1. The triboelectric charge of the compound was +3.9 μC/g.

Example 8

Figure 8:
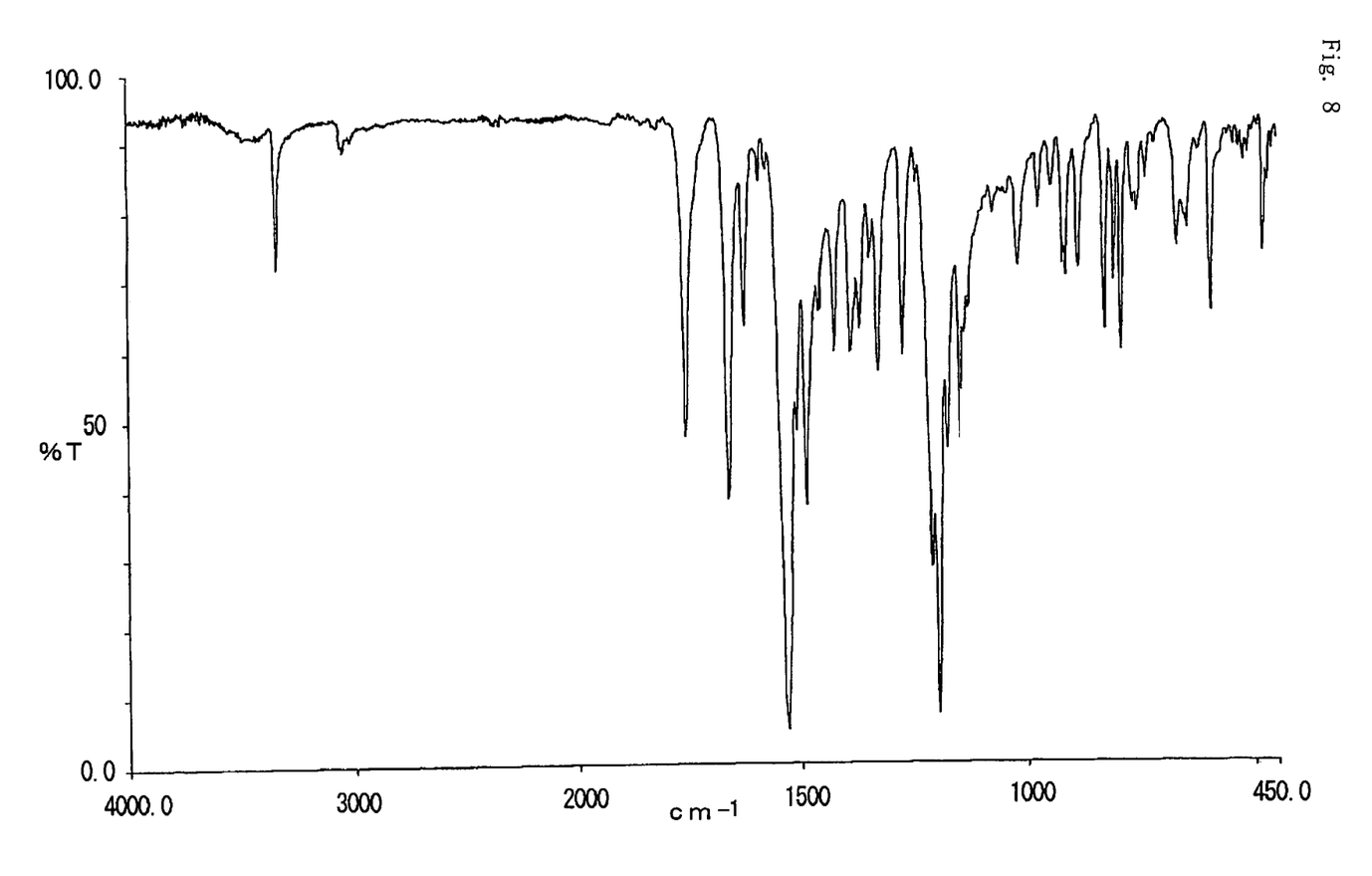
FIG. 8 is an infrared absorption spectrum (KBr) of the compound obtained in Example 8.

16.5 g of 2-acetoxy-6-(quinoline-8-ylaminbcarbonyl) naphthalene (Decomposition point: 341.0° C.) was obtained by the same method as example 1 with the exception that 21.0 g of 8-aminoquinoline was used in stead of 36.0 g of n-dodecyl amine in example 1. The infrared absorption spectrum (KBr) of the compound is shown in FIG. 8. The triboelectric charge was measured by blow-off method as described in example 1. The triboelectric charge of the compound was +5.7 μC/g.

Example 9

Figure 9:
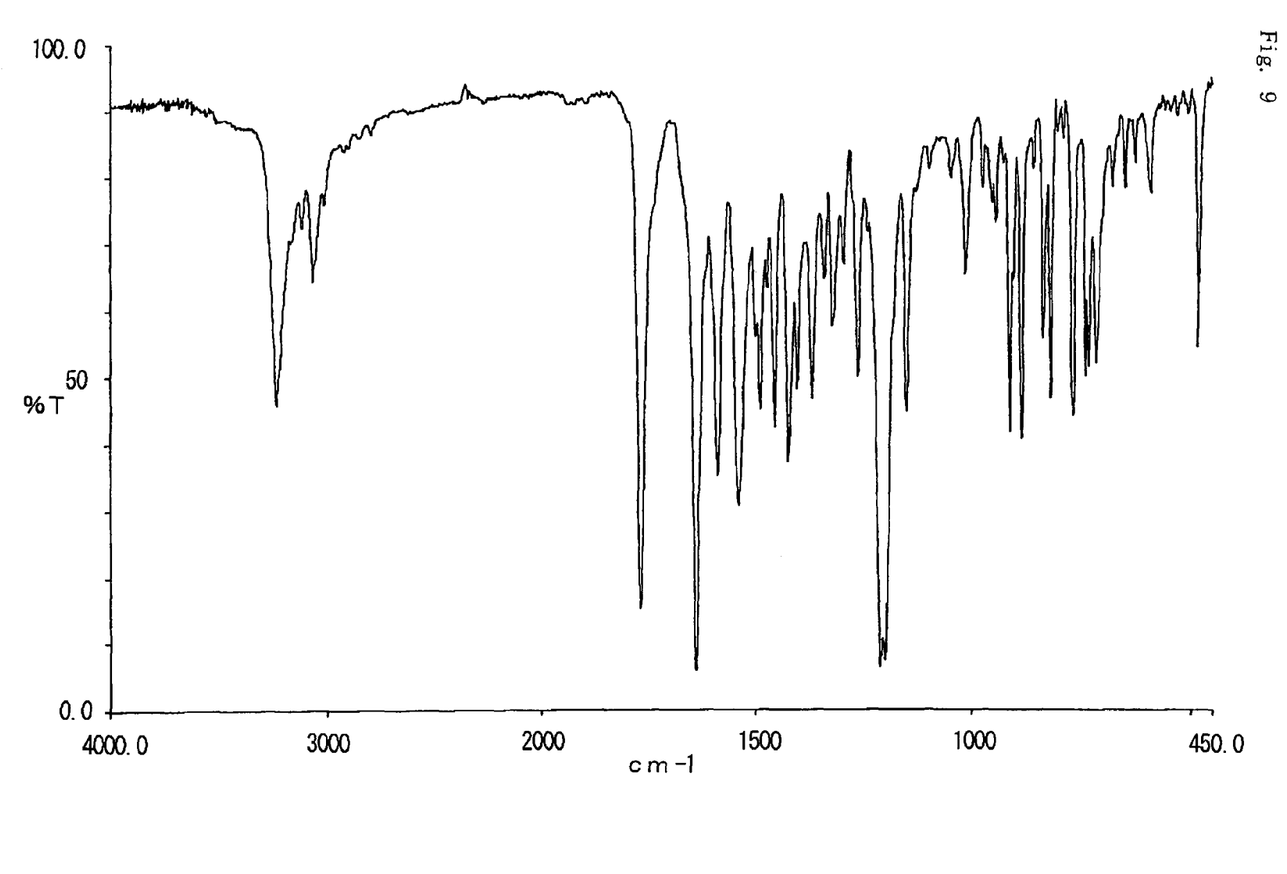
FIG. 9 is an infrared absorption spectrum (KBr) of the compound obtained in Example 9.

27.8 g of 2-acetoxy-6-(fluorene-2-ylaminocarbonyl) naphthalene (Decomposition point: 302.9° C.) was obtained by the same method as example 1 with the exception that 26.4 g of 2-aminofluorene was used instead of 36.0 g of n-dodecyl amine in example 1. The infrared absorption spectrum (KBr) of the compound is shown in FIG. 9. The triboelectric charge was measured by blow-off method as described in example 1. The triboelectric charge of the compound was +16.7 μC/g.

COMPARABLE EXAMPLE 1

The triboelectric charge of BONTRON P-51 (quaternary ammonium salt, Orient Chemical Co., Ltd.) was measured by blow off method as described in example 1. The triboelectric charge of the compound was +1.4 μC/g.

Examples of toner formula are shown below. In the following compositions, "part(S)" means "part(s) by weight".

[Black Toner]

100 parts of Styrene-acrylic resin, 6 parts of carbon black and 2 parts of the compound of Example 1 are preliminary mixed uniformly with the ball mill, and then, the mixture is melt and kneaded with the dispersion kneader. The kneaded mixture is roughly crushed with the vibration mill and further pulverized with the jet mill to give the black toner.

[Color Toner (Cyan)]

Color toner (Cyan) may be prepared in a manner similar to the black toner except for using polyester resin instead of styrene acrylic resin and phthalocyanine blue instead of carbon black.

[Color Toner (Yellow)]

Color toner (Yellow) may be prepared in a manner similar to the black toner except for using polyester resin instead of styrene acrylic resin and Hansa yellow instead of carbon black.

[Color Toner (Magenta)]

Color toner (Magenta) may be prepared in a manner similar to the black toner except for using polyester resin instead of styrene acrylic resin and rose bengal instead of carbon black.

INDUSTRIAL APPLICABILITY

The novel naphthol derivative provided by the present invention can be suitably used as positive charge control agents used for electrophotographic toner and the like.

The invention claimed is:

1. A naphthol derivative represented by the following general formula (I):

[I]

wherein
$R_1$ is an optionally branched, optionally substituted C9 to C20 aliphatic hydrocarbon group which may have an unsaturated bond, and
$R_2$ is a methyl or acetyl group.

2. The naphthol derivative according to claim 1, wherein $R_1$ is an optionally branched, optionally substituted C12 to C18 aliphatic hydrocarbon group.

3. The naphthol derivative according to claim 1, wherein the derivative is positively chargeable and the amount of the charge is no less than +2.0 μC/g.

4. The naphthol derivative according to claim 2, wherein the derivative is positively chargeable and the amount of the charge is no less than +2.0 μC/g.

5. A charge control agent comprising a naphthol derivative represented by formula (I):

[I]

wherein
$R_1$ is an optionally branched, optionally substituted C9 to C20 aliphatic hydrocarbon group which may have an unsaturated bond, and
$R_2$ is a methyl or acetyl group.

6. The charge control agent according to claim 5, wherein $R_1$ is an optionally branched, optionally substituted C12 to C18 aliphatic hydrocarbon group.

7. The charge control agent according to claim 5, wherein the derivative is positively chargeable and the amount of the charge is no less than +2.0 μC/g.

8. The charge control agent according to claim 6, wherein the derivative is positively chargeable and the amount of the charge is no less than +2.0 μC/g.

* * * * *